United States Patent
De La Fuente

(10) Patent No.: US 11,033,354 B1
(45) Date of Patent: *Jun. 15, 2021

(54) STETHOSCOPE SECURING DEVICE

(71) Applicant: Marcus De La Fuente, San Antonio, TX (US)

(72) Inventor: Marcus De La Fuente, San Antonio, TX (US)

( * ) Notice: Subject to any disclaimer, the term of this patent is extended or adjusted under 35 U.S.C. 154(b) by 213 days.

This patent is subject to a terminal disclaimer.

(21) Appl. No.: 16/254,566

(22) Filed: Jan. 22, 2019

Related U.S. Application Data

(63) Continuation-in-part of application No. 15/416,590, filed on Jan. 26, 2017, now Pat. No. 10,182,788.

(51) Int. Cl.
| | | |
|---|---|---|
| *A61B 90/53* | (2016.01) | |
| *A61B 7/02* | (2006.01) | |
| *A61B 90/98* | (2016.01) | |
| *A61B 90/94* | (2016.01) | |
| *A61B 90/00* | (2016.01) | |

(52) U.S. Cl.
CPC ............. *A61B 90/53* (2016.02); *A61B 7/02* (2013.01); *A61B 90/94* (2016.02); *A61B 90/98* (2016.02); *A61B 2090/0807* (2016.02)

(58) Field of Classification Search
CPC ......... A61B 90/53; A61B 90/98; A61B 90/94; A61B 2090/0807; A61B 7/02
USPC ...................................................... 181/131
See application file for complete search history.

(56) References Cited

U.S. PATENT DOCUMENTS

| | | | | |
|---|---|---|---|---|
| 4,406,042 A | * | 9/1983 | McPhee | A61M 5/1418 24/129 A |
| 4,637,075 A | * | 1/1987 | Ingrisano | A41D 13/0012 2/102 |
| 5,451,725 A | * | 9/1995 | Goldman | A45F 5/02 181/131 |
| 5,798,489 A | * | 8/1998 | Gillio | A61B 7/02 181/131 |
| 6,065,563 A | * | 5/2000 | Stowers | A45F 5/02 181/131 |
| 6,286,147 B1 | * | 9/2001 | Ingold | A41D 13/0012 2/114 |
| 9,289,051 B1 | * | 3/2016 | Capps | A45F 3/005 |
| 10,182,788 B2 | * | 1/2019 | De La Fuente | F16B 1/00 |
| 2006/0201738 A1 | * | 9/2006 | Krysztof | G09F 3/00 181/131 |

(Continued)

*Primary Examiner* — Forrest M Phillips
(74) *Attorney, Agent, or Firm* — Taboada Law Firm, PLLC; John M. Taboada

(57) ABSTRACT

The present invention is a novel device that improves the user's ability to carry or store a stethoscope while it is not in use, thereby enhancing the security of the stethoscope by preventing and reducing falls and collisions. In one embodiment, a device comprises two reversibly connectable connector sections that can be attached at different points along the stethoscope, such that a stable closed loop can be formed when the two sections are in the connected position. The sections can be unconnected easily by the user when the stethoscope is desired to be used, but resists unintended or accidental disconnection. In another embodiment, the device also enhances the ability of a user to identify the stethoscope by providing a surface for tags, text, or images. In other embodiments, embedded electronics provide enhanced tracking and communication options.

14 Claims, 16 Drawing Sheets

(56) References Cited

U.S. PATENT DOCUMENTS

| | | | | |
|---|---|---|---|---|
| 2006/0219472 A1* | 10/2006 | Vance | ................. | A61B 7/02 |
| | | | | 181/131 |
| 2009/0026237 A1* | 1/2009 | Weaver | ................. | A45F 5/02 |
| | | | | 224/269 |
| 2011/0010895 A1* | 1/2011 | Ream | ................. | A61B 7/02 |
| | | | | 24/129 R |
| 2016/0192846 A1* | 7/2016 | Shekhar | ................. | A61B 7/02 |
| | | | | 600/528 |

\* cited by examiner

STETHOSCOPE SECURING DEVICE

I. CROSS REFERENCE TO RELATED APPLICATIONS

The application is a continuation-in-part application of U.S. Pat. No. 10,182,788, titled "Stethoscope Securing Device," filed Jan. 26, 2017, the entire disclosure of which is hereby incorporated by reference into the present disclosure.

II. SUMMARY

The present invention is a novel device that improves the user's ability to carry a stethoscope during non-use. The device also enhances the security of the stethoscope by preventing and reducing falls and collisions. The invention also prevents unwanted contact of the instrument with foreign surfaces. In various embodiments described below, the device also enhances the ability of a user to identify the stethoscope. In other embodiments, the device also enhances communication and management.

In short, it is a goal of the present invention to provide a novel solution to the problems discussed in the Background section above by adding a reversibly connectable connector to the stethoscope in a manner that has never been conceived let alone done before. Despite the many problems discussed above, nothing similar to the present invention is available on the market.

It is a most basic goal of the present invention to form at least one closed loop by connecting two distal points of the stethoscope to one another. It is a goal that the circumference of this loop can be adjusted by adjusting the two distal points at which the invention is positioned.

It is another goal that the connecting method is readily reversibly and repeatable.

It is a goal of the present invention to offer easy single handed access to the stethoscope.

It is yet another goal that the invention does not cause damage or wear on the stethoscope when the invention's features are used.

It is still another goal that the invention provides a surface for information (text, images, etc.) useful for identification and tracking of the stethoscope.

It is a goal that the invention does not require the user to wear special clothing. It is a goal that the invention does not consist of large, bulky, or heavy parts.

It is a goal that the invention can be left attached to the stethoscope at all times and does not require the user to perform additional tasks beyond the initial application of the device.

It is a goal that the invention be easy to remove and clean when desired.

Additional features, goals, and advantages of this invention will be readily understood from the following descriptions, drawings, and claims.

III. BACKGROUND

Many professionals operating in the field of healthcare utilize medical devices and tools on a daily basis. These professionals often carry with them certain staple instruments throughout the day. Among the staple instruments, a particularly common instrument is the stethoscope. Unfortunately, many users find the stethoscope to be as cumbersome to carry as it is useful. The gangly device cannot be crushed or sharply folded. Carrying it in one's pocket is typically impossible or impractical. Its unbalanced weight distribution causes shifts and sliding when draped over necks, shoulders, and wall hooks. Left unsecured the dangling chest piece becomes a war mace inflicting damage on the user's body and surrounding objects. The frequent drops and collisions cause damage to the device itself which is expensive to repair or replace. Professionals working in the fast pace environment of emergency rooms, or in flight and mobile nursing, and those working as first responders know these problems all too well. Military and civilian medical teams working in the military must have secure rapid access to their instruments due to the stressful and highly physical environment they may be deployed in. First responders, emergency services personnel, and military staff may also be in uniforms that are bulky or burdened with other gear limiting quick or secure access. On the flipside, hospital and clinic staff may be in uniforms such as scrubs with poorly designed or inadequate pockets. Setting the instrument down is not an alternative as the user must always have their instruments ready for use. Yet in the course of a single shift, the user may reach for, use, and then put away an instrument many dozens of times. Anything that can reduce that burden will improve both the performance of the user and the quality of the care they can deliver.

In addition to those concerns, many users desire to carry the stethoscope or other instrument in a secured manner for reasons of hygiene. In the environments where users are working, diseases are often transmitted through contact with surface pathogens found on counters, stretchers, gurneys, chairs, tables, doorknobs, and floors. Earpieces or ear tips in particular can collect debris, bacteria, viral mater, mold, etc. from contact with foreign surfaces. Upon use, the ear tips will then make contact with the user's ear canal raising the likelihood of contamination. The chest piece may also act as a carrier cross contaminating patients and professionals. It becomes a vital part of the user's hygiene strategy to keep instruments secured and away from unnecessary contact with such foreign surfaces.

For all of those reasons and many more industrious inventors have strived for an improved method of carrying instruments such as the stethoscope.

Some inventions sought to address the problem by attaching the stethoscope to the user's clothing. See U.S. Pat. Nos. 5,451,725, 5,692,657, 6,065,563, 6,286,147, 6,419,133, 9,009,922, and US2009026237. There are some downsides to these devices that can't be overlooked. In the case of U.S. Pat. Nos. 5,692,657, 6,065,563, 6,419,133, and 9,009,922, a bulky holster is required. Holsters may not secure well to scrub pants and other unbelted outfits. Holsters are also prone to catching on furniture and other people. In U.S. Pat. No. 6,286,147, the stethoscope is secured by the user's garment itself which has specially designed features. The user is unable to secure the stethoscope unless they are wearing that special garment. In patent application US2009026237, the disclosed device required the user to first install a magnetically drawn set of plates inside and outside of the user's clothing at the location where the user intended to secure the stethoscope. Some perceived problems include: the extra bulk and weight of the magnetic plates on the user's clothing; the plates have to be strong enough to not be pulled apart when the user attempts to detach the stethoscope; the need to remove the device from each garment after each wear by the user; and the potential failure of the device on thick clothing, to name a few.

U.S. Pat. No. 9,289,051 sought to secure the stethoscope as part of a utility belt. This may be an ideal situation for certain heroes of the medical profession, however many professionals don't need to carry a large array of instruments. The ideal invention would be light, efficient, easy to use, hard to lose, and effectively secure the stethoscope regardless of the user's attire. Patent application US20110010895 sought to meet this need by using a modified "s" hook configured foam tube clip. That application was rejected in light of expired U.S. Pat. No. 4,406,042 which was for "s" hook tube clips. The problem with pulling the stethoscope in and out of such a clip is that it is likely to cause wear and tear on the tubing over time. The use of foam construction may have been meant to address this problem, but created new ones. The resiliency of foam degrades over repeated use, thereby likely leading to failure or weakening of the grip on the tubing and consequently unintended releases of the tubing. It would be quite dangerous to have the stethoscope drop into a patient during surgery, or swing into a child's face during an examination. A user perceiving there was a risk for such an unintended release would hesitate to continue using such a product.

Another concern shared by medical professionals and medical facilities is the misplacement and displacement of instruments such as stethoscopes. If a user spends good money to get a high performance instrument, they will seek to protect it from being lost or taken by mistake. Likewise, medical facilities may have instruments that they own and maintain. These facilities may desire a means to readily identify their property.

U.S. Pat. No. 6,701,648 disclosed a locking stethoscope identification tag. This consisted of essentially two plates that would adjustably lock upon being pressed together over a section of the binaural spring and sound conductor fork. The outward facing plate provided a location for placing identification information. While that prior art accomplishes the goal of providing a surface for labeling and identifying, it does nothing to add to the securing of the stethoscope while the user is carrying it.

IV. BRIEF DESCRIPTION OF THE DRAWINGS

Figure 12:
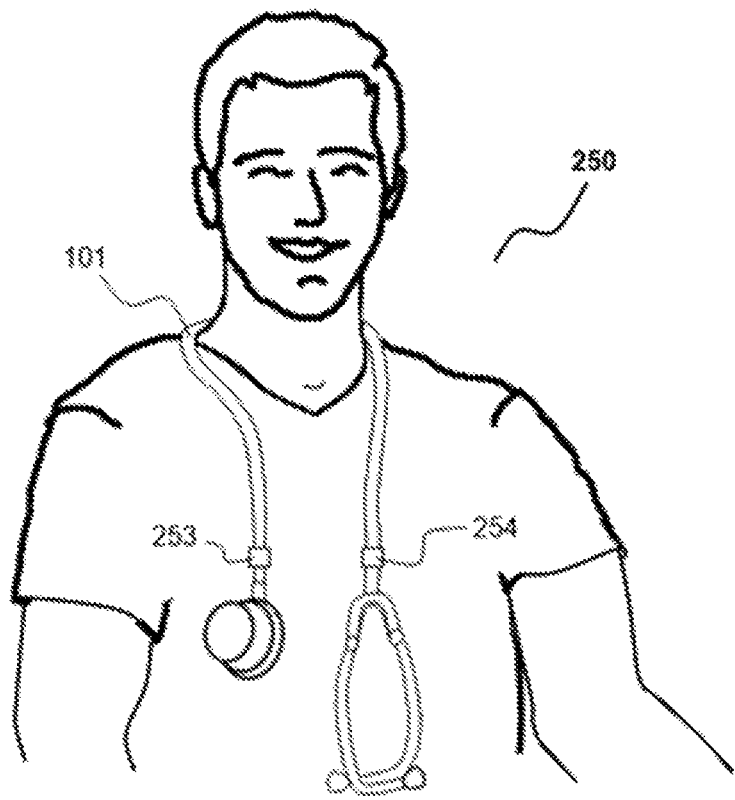

FIG. 12 shows a user wearing a stethoscope draped over the user's shoulder and behind the user's neck, wherein the stethoscope is equipped with an embodiment of the invention positioned on the stethoscope such that one piece of the connector is on a section of the stethoscope tube and the other piece is on a distal section of the stethoscope tube, further wherein the connector is in the unconnected position.

Figure 13:
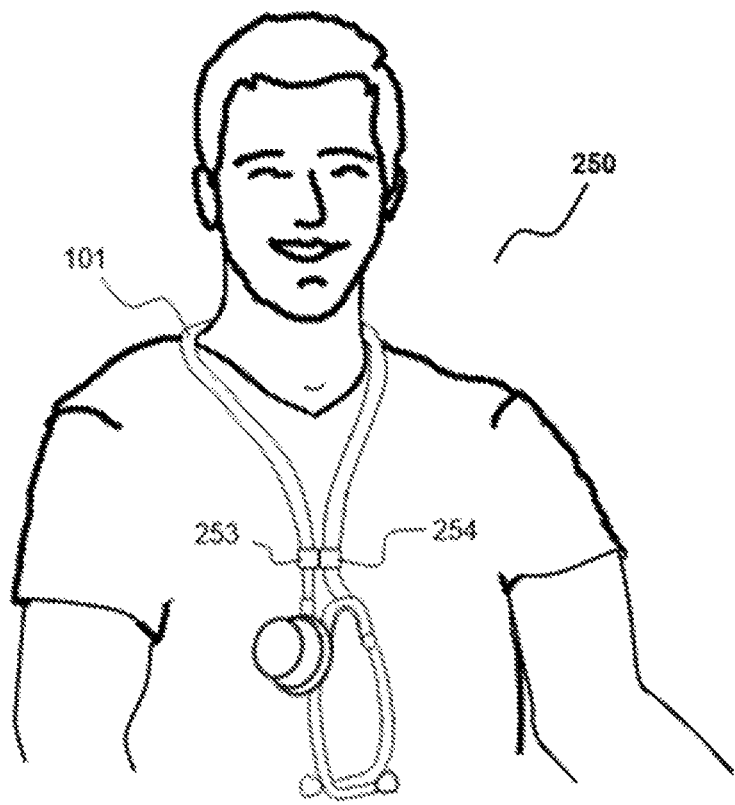

FIG. 13 shows a user wearing a stethoscope draped over the user's shoulder and behind the user's neck, wherein the stethoscope is equipped with an embodiment of the invention positioned on the stethoscope such that one piece of the connector is on a section of the stethoscope tube and the other piece is on a distal section of the stethoscope tube, further wherein the connector is in the connected position.

Figure 14:
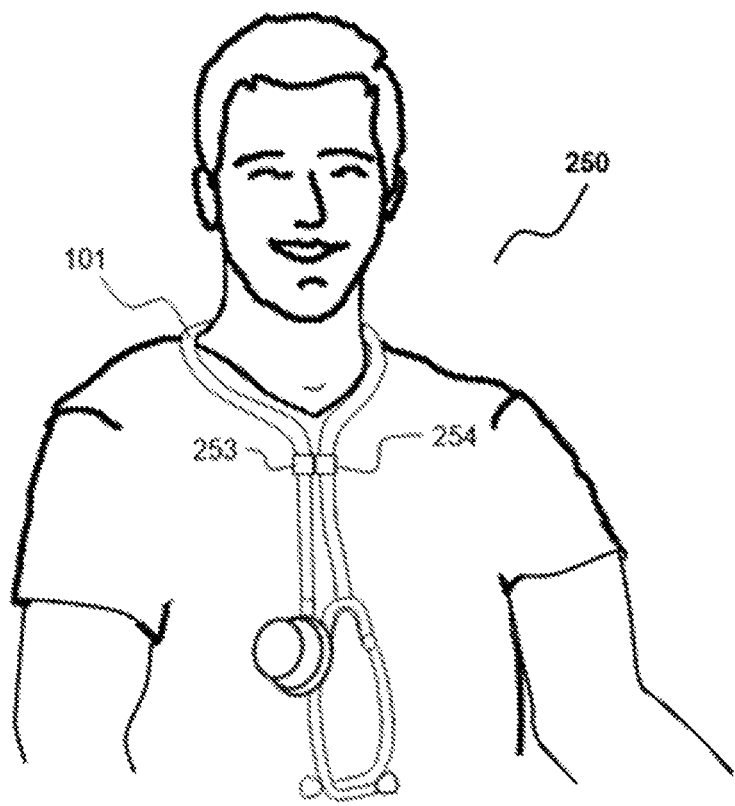

FIG. 14 repeats FIG. 13 but shows that each piece of the connected connector has been moved to a new position less distal relative to one another along the length of the stethoscope tube than shown in FIG. 13.

Figure 15:
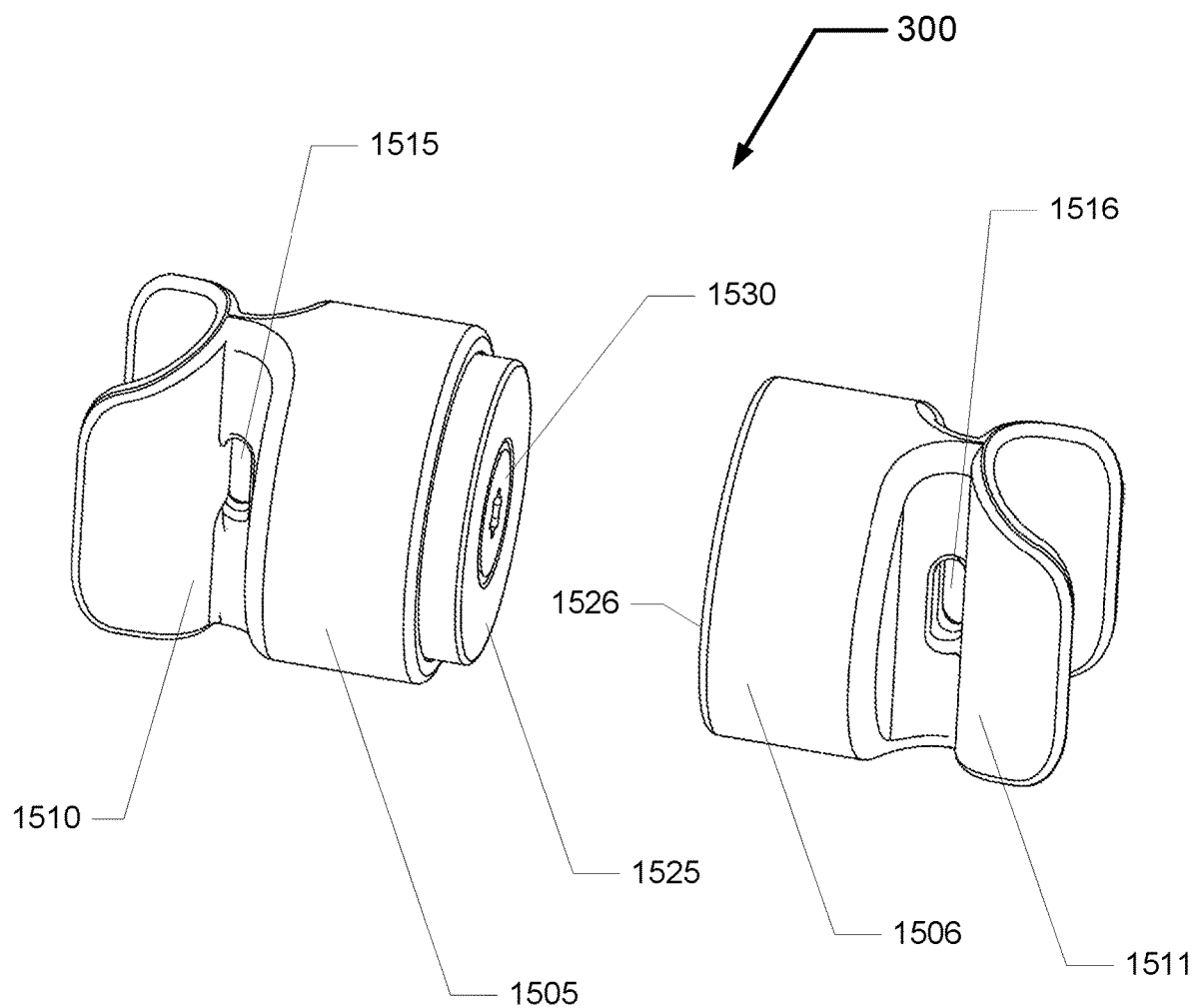

FIG. 15 shows a stethoscope securing device, in accordance with some embodiments.

Figure 16:
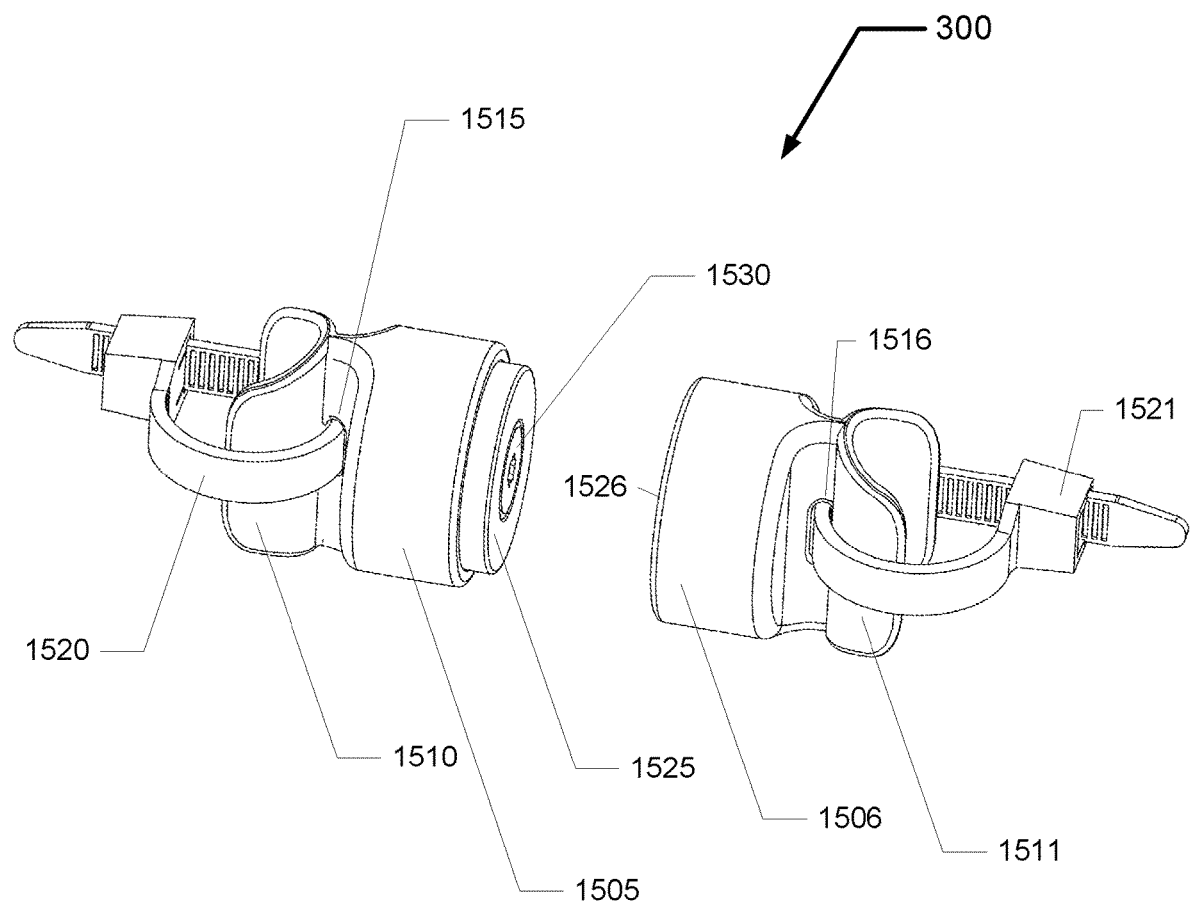

FIG. 16 shows the stethoscope securing device of FIG. 15 with cable ties, in accordance with some embodiments.

V. DETAILED DESCRIPTION

The invention disclosed herein will be described according to various embodiments to illustrate particular features and functionality. Since this invention is particularly well suited for the stethoscope, it is worth noting here the basic parts typical of this instrument. The typical stethoscope comprises two eartips formed on a binaural. In between the two eartips, is a sound conductor. There is a spring clamp that is attached to the binaural at a location centered around the sound conductor. A flexible tube extends from the sound conductor to an acoustic valve stem. The valve stem is attached to a chestpiece comprising at least one bell for detecting acoustic or vibration frequencies.

Figure 1:
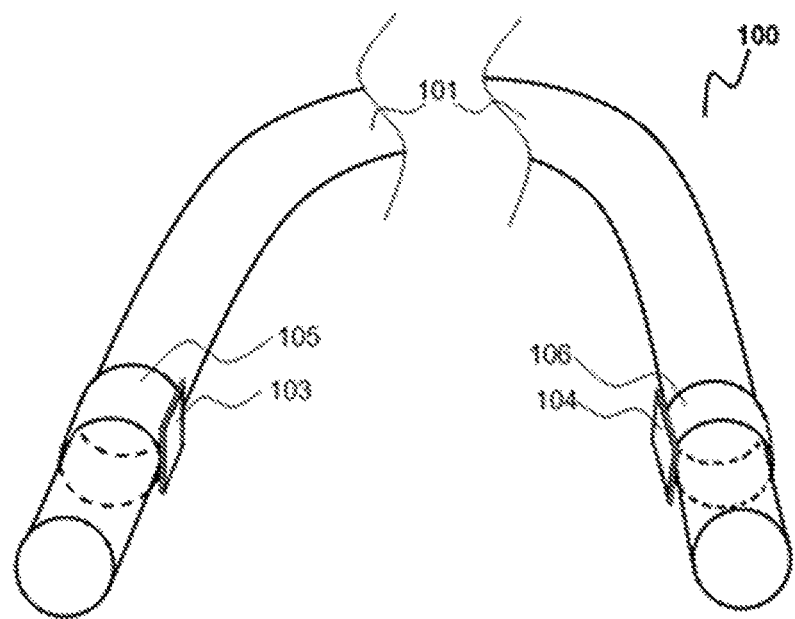
FIG. 1 shows a basic embodiment of the invention comprising two sections of a reversibly connectable connector in an unconnected position on two distal locations of a stethoscope tube.

Referring to FIG. 1 a first embodiment, device 100, is shown attached to a stethoscope 101 (not fully depicted). Device 100 comprises a body having a reversibly connectable connector. Connector comprises a first section 103 and a second section 104, wherein the first section 103 is attached to a first location on the stethoscope via an attachment member 105 and the second section 104 is attached to a second location on the stethoscope via an attachment member 106. FIG. 1 shows device 100 in a first configuration where the connector sections (103, 104) are unconnected.

A user can first attach the device 100 to the stethoscope 101 via the attachment members (105, 106). Next, an optimal first and second location for sections 103 and 104, respectively, is set by the user according to the user's needs or desires. If the user desires to secure the stethoscope around their own neck, the user can hang the stethoscope around their neck and adjust the first and second locations such that the two locations can be comfortably brought together and connected via connector. When connector is connected it is in a second configuration that forms a closed loop with the stethoscope. The closed loop will keep the stethoscope secured to the user's neck as the user moves about, preventing damage or unwanted contact with foreign surfaces. Alternatively, the stethoscope 101 and connector can be put into the second configuration forming a closed loop, when not around a user's neck. This makes the stethoscope easier to hang on a hook or peg, to carry around, or to store in a drawer.

Figure 2:
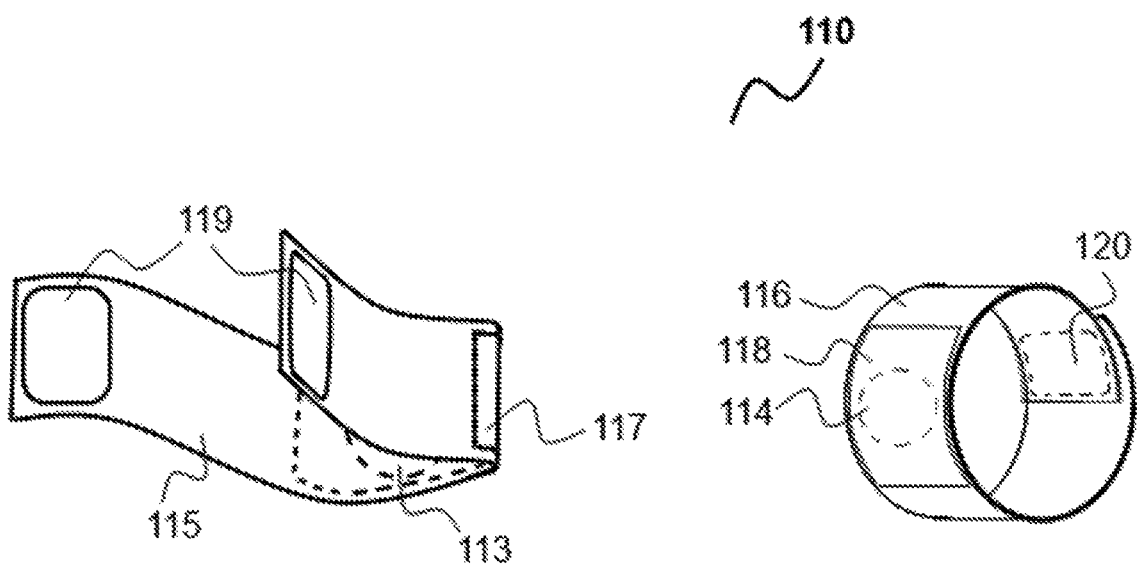
FIG. 2 shows another basic embodiment of the invention comprised of two sections of a reversibly connectable connector in an unconnected position. One of the sections is shown with the tube attachment band open, while the other is shown with the tube attachment band closed.
Figure 3:
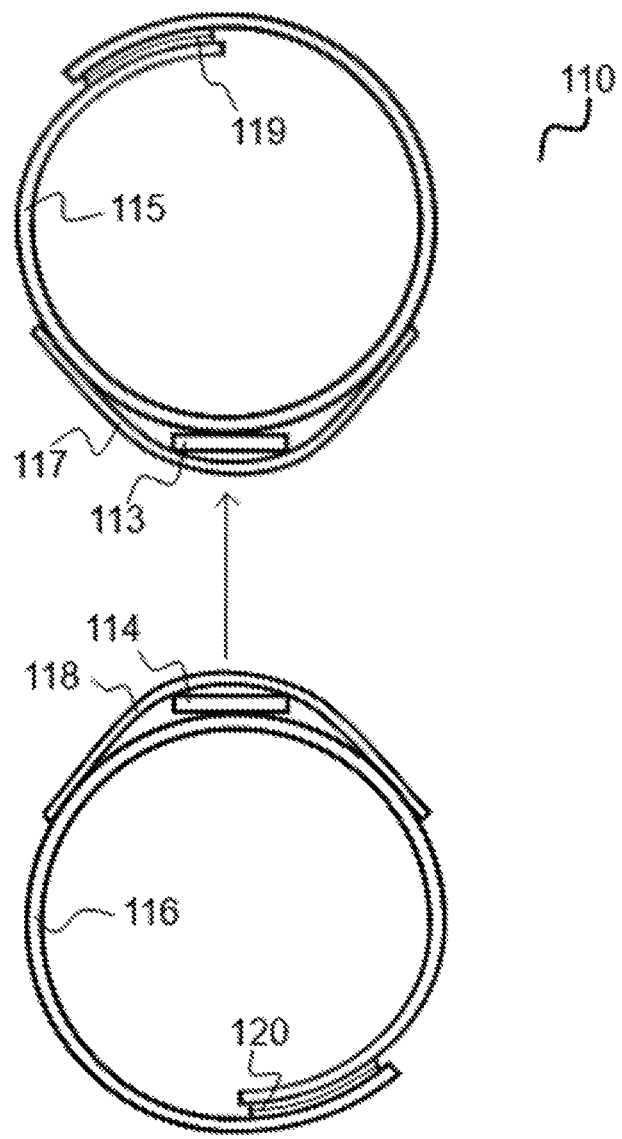
FIG. 3 shows an axial viewpoint cross section of a basic embodiment of the invention showing how the addition of a retaining layer to the tube attachment band creates a pocket wherein a magnet is positioned.

Referring now to FIG. 2 and FIG. 3, another embodiment, device 110, is shown. Device 110 comprises a reversibly connectable magnetic connector. Connector comprises a first section 113 and a second section 114. Device 110 further comprises an attachment band 115, an attachment band 116, a retaining layer 117, and a retaining layer 118. Retaining layer 117 is attached to the attachment band 115 such that the first section 113 of connector is positioned between the retaining layer and the attachment band. See FIG. 3. Retaining layer 118 is attached to the attachment band 116 such that the second section 114 of connector is positioned between the retaining layer and the attachment band.

The first section 113 is attached to a stethoscope by a user at a first location on the stethoscope via the attachment band 115 and the second section 114 is attached at a second location on the stethoscope via the attachment band 116. The user attaches attachment band 115 by first opening band fastener 119, then wrapping attachment band 115 around the first location on the stethoscope, and finally closing band fastener 119. The same operation is repeated for attaching attachment band 116 at the second location on the stethoscope by using band fastener 120. FIG. 2 shows band fastener 119 in the open position and band fastener 120 in the closed position. FIG. 2 and FIG. 3 show device 110 in a first configuration where the connector sections (113, 114) are unconnected.

There are many well known methods of attachment and many well know fastener types that would be readily apparent to one having ordinary skill in the art. Each may be a suitable replacement or substitution for the other, or there may be inherent advantages to one method of attachment and fastener type depending on the situation. Still referring to device 110, take as example and not limitation the following construction: the connector could be a simple pair of magnetic disks; the attachment band and retaining layer could be constructed of a durable fabric material such as nylon or cotton; the retaining layer could be sewed onto the attachment band; and the band fastener could be constructed of hook and loop style fasteners sewed onto the attachment band.

Figure 4:
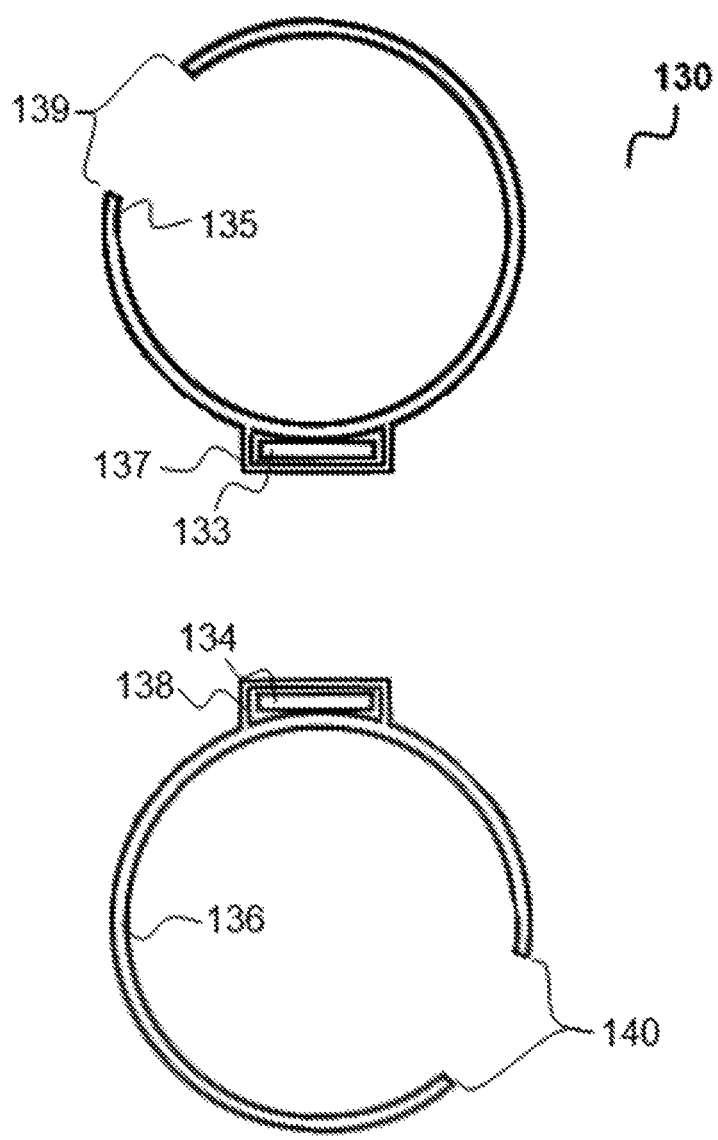
FIG. 4 shows an axial viewpoint cross section of a basic embodiment of the invention showing a pocket, wherein a magnet is positioned, formed into a tube attachment clip.

Referring now to FIG. 4, another embodiment, device 130, is shown. Device 130 comprises a reversibly connectable magnetic connector. Connector comprises a first section 133 and a second section 134. Device 130 further comprises an attachment clip 135, an attachment clip 136, a retaining layer 137, and a retaining layer 138. Retaining layer 137 is attached to the attachment clip 135 such that the first section 133 of connector is positioned between the said retaining layer and the said attachment clip. Retaining layer 138 is attached to the attachment clip 136 such that the second section 134 of connector is positioned between the said retaining layer and the said attachment clip. Attachment clip 135 has clip opening 139, wherein the said opening is sufficiently wide to allow the stethoscope tube to pass through. The tube may require the user to apply force and deform the tube to pass into attachment clip 135. The attachment clip 135 may also require temporary deformation to allow the tube to pass through the clip opening 139. Attachment clip 136 has clip opening 140, wherein the said opening is sufficiently wide to allow the stethoscope tube to pass through, but may require force and temporary deformation of the attachment clip 136 and the tube. The opening 139 should not be located opposite the first section 133 of the connector. The opening 140 should not be located opposite the second section 134 of the connector.

The first section 133 is attached to a stethoscope by a user at a first location on the stethoscope via the attachment clip 135 and the second section 134 is attached at a second location on the stethoscope via the attachment clip 136. The user attaches attachment clip 135 by gently forcing the section of the stethoscope at the first location on the stethoscope through the clip opening 139. The same operation is repeated for attaching attachment clip 136 at the second location on the stethoscope using clip opening 140. FIG. 4 shows device 130 in a first configuration where the connector sections (133, 134) are unconnected.

There are many well known methods of attachment and many well know fastener types that would be readily apparent to one having ordinary skill in the art. Each may be a suitable replacement or substitution for the other, or there may be inherent advantages to one method of attachment and fastener type depending on the situation. Still referring to device 130, take as example and not limitation the following construction: the connector could be a simple pair of magnetic disks; the attachment clip and retaining layer could be constructed of a durable plastic, wood, or metal material; and the retaining layer could be formed into the attachment clip or glued, soldered, welded, fused, screwed, etc. onto the attachment clip.

Figure 5:
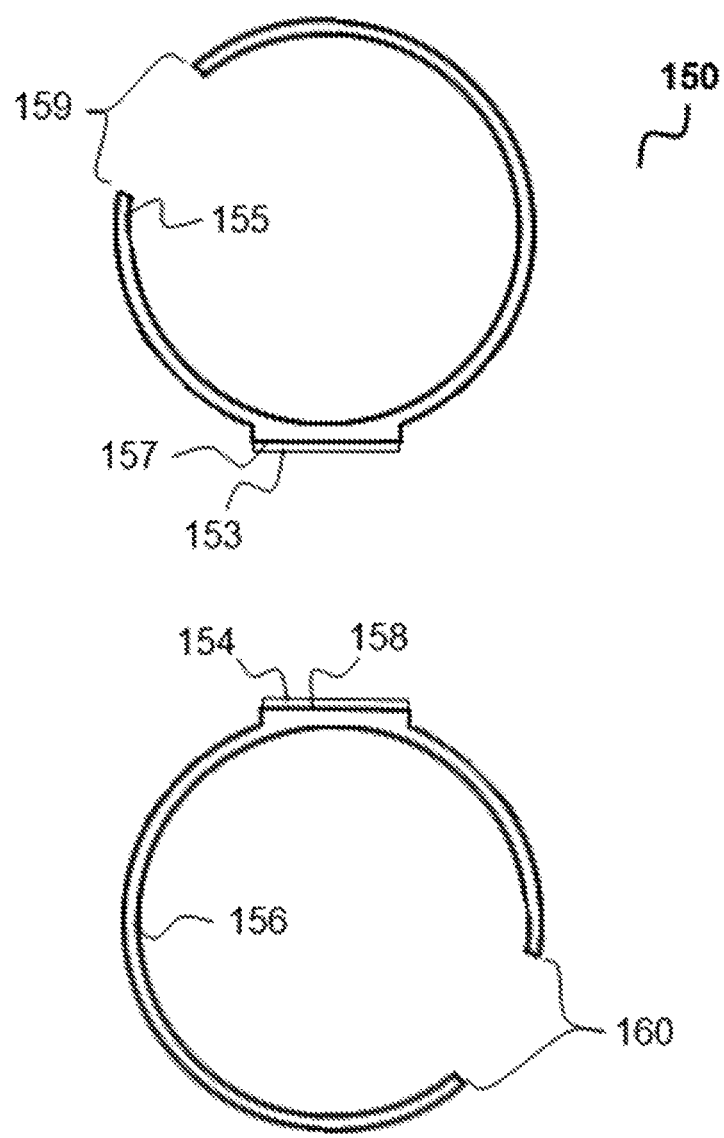
FIG. 5 shows an axial viewpoint cross section of a basic embodiment of the invention showing a substantially tangential surface, whereupon an adhesive or hook and loop style connector is positioned, formed onto a tube attachment clip.

Referring now to FIG. 5, another embodiment, device 150, is shown. Device 150 comprises a reversibly connectable connector. Connector comprises a first section 153 and a second section 154. Device 150 further comprises an attachment clip 155, an attachment clip 156, a surface 157, and a surface 158. Surface 157 is formed into the attachment clip 155 and attaches to first section 153. Surface 158 is formed into the attachment clip 156 and attaches to second section 154. Attachment clip 155 has clip opening 159, wherein the said opening is sufficiently wide to allow the stethoscope tube to pass through. The tube may require the user to apply force and deform the tube to pass into attachment clip 155. The attachment clip 155 may also require temporary deformation to allow the tube to pass through the clip opening 159. Attachment clip 156 has clip opening 160, wherein the said opening is sufficiently wide to allow the stethoscope tube to pass through, but may require force and temporary deformation of the attachment clip 156 and the tube. The opening 159 should not be located opposite the first section 153 of the connector. The opening 160 should not be located opposite the second section 154 of the connector.

The first section 153 is attached to a stethoscope by a user at a first location on the stethoscope via the attachment clip 155 and the second section 154 is attached at a second location on the stethoscope via the attachment clip 156. The user attaches attachment clip 155 by gently forcing the section of the stethoscope at the first location on the stethoscope through the clip opening 159. The same operation is repeated for attaching attachment clip 156 at the second location on the stethoscope using clip opening 160. FIG. 5 shows device 150 in a first configuration where the connector sections (153, 154) are unconnected.

There are many well known methods of attachment and many well know fastener types that would be readily apparent to one having ordinary skill in the art. Each may be a suitable replacement or substitution for the other, or there may be inherent advantages to one method of attachment and fastener type depending on the situation. Still referring to device 150, take as example and not limitation the following construction: the connector could be a simple pair of magnetic disks or a patch of hook and loop material; the attachment clip and surface could be constructed of a durable plastic, wood, or metal material; and the connector sections (153, 154) could be formed into the surfaces (157, 158) or glued, soldered, welded, fused, screwed, etc. onto said surfaces.

Figure 6:
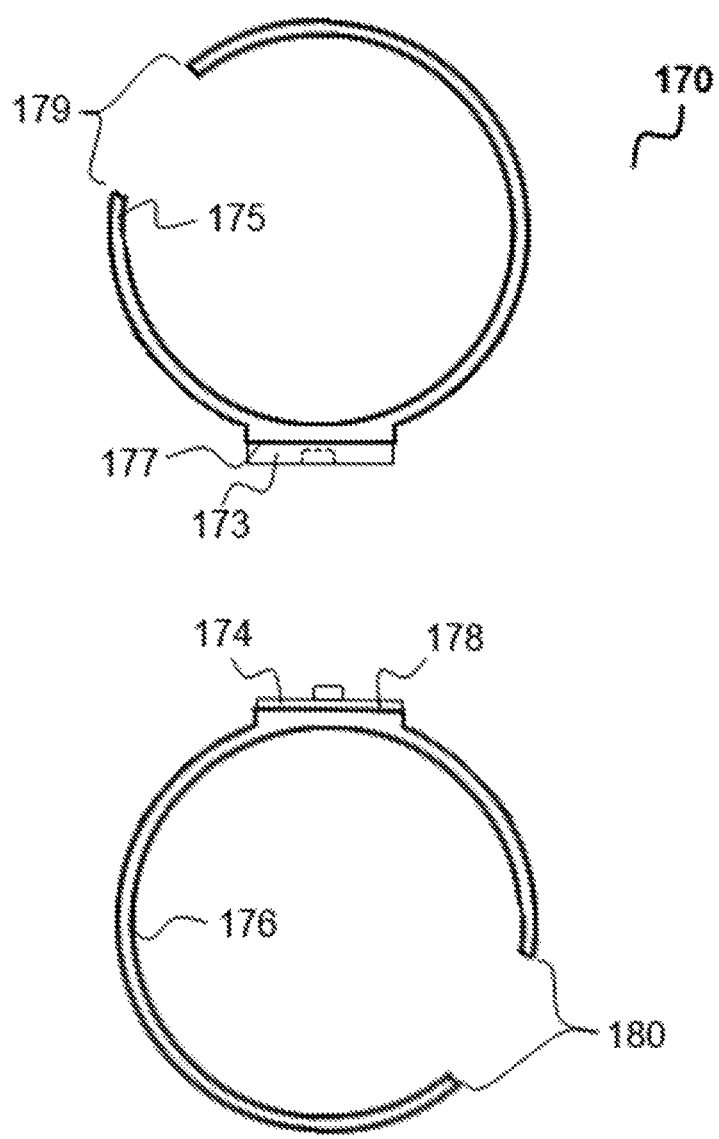
FIG. 6 shows an axial viewpoint cross section of a basic embodiment of the invention showing a substantially tangential surface, whereupon a snap button style connector is positioned, formed onto a tube attachment clip.

Referring now to FIG. 6, another embodiment, device 170, is shown. Device 170 comprises a reversibly connectable button snap connector. Connector comprises a first section 173 and a second section 174. Device 170 further comprises an attachment clip 175, an attachment clip 176, a surface 177, and a surface 178. Surface 177 is formed into the attachment clip 175 and attaches to first section 173. Surface 178 is formed into the attachment clip 176 and attaches to second section 174. Attachment clip 175 has clip opening 179, wherein the said opening is sufficiently wide to allow the stethoscope tube to pass through. The tube may require the user to apply force and deform the tube to pass into attachment clip 175. The attachment clip 175 may also require temporary deformation to allow the tube to pass through the clip opening 179. Attachment clip 176 has clip opening 180, wherein the said opening is sufficiently wide to allow the stethoscope tube to pass through, but may require force and temporary deformation of the attachment clip 176 and the tube. The opening 179 should not be located opposite the first section 173 of the connector. The opening 180 should not be located opposite the second section 174 of the connector.

The first section 173 is attached to a stethoscope by a user at a first location on the stethoscope via the attachment clip 175 and the second section 174 is attached at a second location on the stethoscope via the attachment clip 176. The user attaches attachment clip 175 by gently forcing the section of the stethoscope at the first location on the stethoscope through the clip opening 179. The same operation is repeated for attaching attachment clip 176 at the second location on the stethoscope using clip opening 180. FIG. 6 shows device 170 in a first configuration where the connector sections (173, 174) are unconnected.

There are many well known methods of attachment and many well know fastener types that would be readily apparent to one having ordinary skill in the art. Each may be a suitable replacement or substitution for the other, or there may be inherent advantages to one method of attachment and fastener type depending on the situation. Still referring to device 170, take as example and not limitation the following construction: the connector could be a simple button snap; the attachment clip and surface could be constructed of a durable plastic, wood, or metal material; and the connector sections (173, 174) could be formed into the surfaces (177, 178) or glued, soldered, welded, fused, screwed, etc. onto said surfaces.

Figure 7:
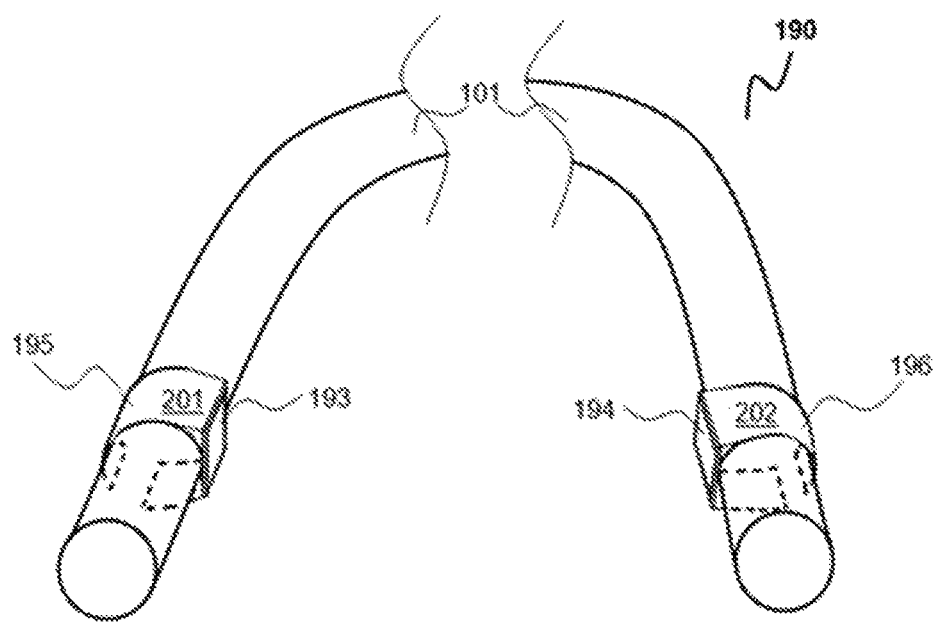
FIG. 7 shows an embodiment of the invention comprised of two sections of a reversibly connectable connector in an unconnected position on two distal locations of a stethoscope tube, wherein each section comprises a tube attachment clip that has a substantially tangential outer wall such that the outer wall is also substantially perpendicular to the connector's plane of connection.

Referring now to FIG. 7, another embodiment, device 190, is shown. Device 190 is largely similar to device 150 in that it comprises a reversibly connectable connector. Connector comprises a first section 193 and a second section 194. Device 190 also comprises an attachment clip 195, an attachment clip 196, a surface 201, and a surface 202. Surface 201 is formed into the attachment clip 195 and attaches to first section 193. Surface 202 is formed into the attachment clip 196 and attaches to second section 194. Attachment clip 195 has clip opening, wherein the said opening is sufficiently wide to allow the stethoscope tube to pass through. The tube may require the user to apply force and deform the tube to pass into attachment clip 195. The attachment clip 195 may also require temporary deformation to allow the tube to pass through the clip opening. Attachment clip 196 has clip opening, wherein the said opening is sufficiently wide to allow the stethoscope tube to pass through, but may require force and temporary deformation of the attachment clip 196 and the tube. The opening of attachment clip 195 should not be located opposite the first section 193 of the connector. The opening of attachment clip 196 should not be located opposite the second section 194 of the connector.

However, unlike device 150, device 190 further comprises an outer wall 201 of attachment clip 195 and an outer wall 202 of attachment clip 196. The outer wall 201 is substantially tangential to the attachment clip 195 and substantially perpendicular to the first section 193 of connector. The outer wall 202 is substantially tangential to the attachment clip 196 and substantially perpendicular to the second section 194 of connector.

The first section 193 is attached to a stethoscope by a user at a first location on the stethoscope via the attachment clip 195 and the second section 194 is attached at a second location on the stethoscope via the attachment clip 196. The user attaches attachment clip 195 by gently forcing the section of the stethoscope at the first location on the stethoscope through the clip opening of attachment clip 196. The same operation is repeated for attaching attachment clip 196 at the second location on the stethoscope using clip opening of attachment clip 195. FIG. 7 shows device 190 in a first configuration where the connector sections (193, 194) are unconnected.

There are many well known methods of attachment and many well know fastener types that would be readily apparent to one having ordinary skill in the art. Each may be a suitable replacement or substitution for the other, or there may be inherent advantages to one method of attachment and fastener type depending on the situation. Still referring to device 150, take as example and not limitation the following construction: the connector could be a simple pair of magnetic disks or a patch of hook and loop material; the attachment clip and surface could be constructed of a durable plastic, wood, or metal material; and the connector sections (193, 194) could be formed into the surfaces or glued, soldered, welded, fused, screwed, etc. onto said surfaces.

Figure 8:
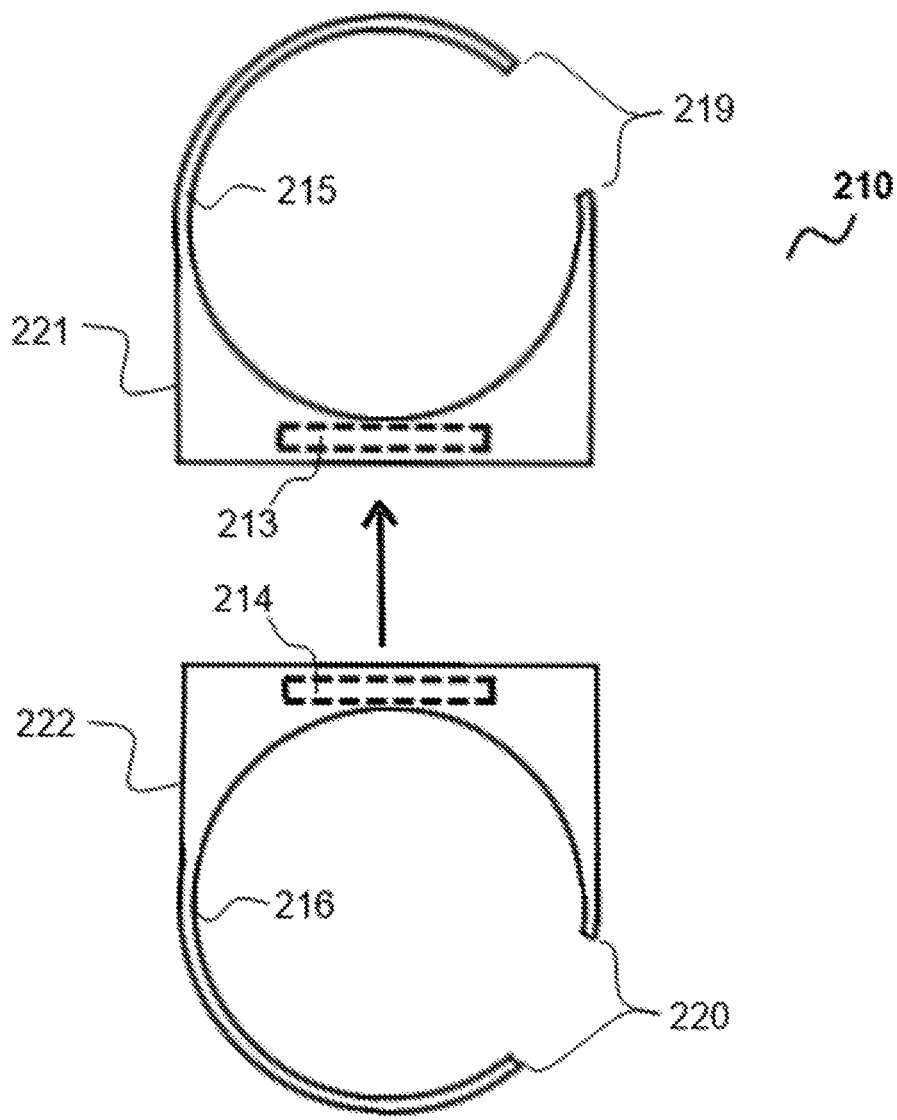
FIG. 8 shows an axial viewpoint cross section of an embodiment of the invention showing a pocket, wherein a magnet is positioned, formed into a tube attachment clip having an outer wall that is substantially tangential to the tube attachment clip and substantially perpendicular to the connector's plane of connection.

Referring now to FIG. 8, another embodiment, device 210, is shown. Device 210 is largely similar to device 130 in that it comprises a reversibly connectable magnetic connector. Connector comprises a first section 213 and a second section 214. Device 210 further comprises an attachment clip 215, an attachment clip 216, a retaining layer of attachment clip 215, and a retaining layer of attachment clip 216. Retaining layer of attachment clip 215 is attached to the attachment clip 215 such that the first section 213 of connector is positioned between the said retaining layer and the said attachment clip. Retaining layer of attachment clip 216 is attached to the attachment clip 216 such that the second section 214 of connector is positioned between the said retaining layer and the said attachment clip. Attachment clip 215 has clip opening 219, wherein the said opening is sufficiently wide to allow the stethoscope tube to pass through. The tube may require the user to apply force and deform the tube to pass into attachment clip 215. The attachment clip 215 may also require temporary deformation to allow the tube to pass through the clip opening 219. Attachment clip 216 has clip opening 220, wherein the said opening is sufficiently wide to allow the stethoscope tube to pass through, but may require force and temporary deformation of the attachment clip 216 and the tube. The opening 219 should not be located opposite the first section 213 of the connector. The opening 220 should not be located opposite the second section 214 of the connector.

However, unlike device 130, device 210 further comprises an outer wall 221 of attachment clip 215 and an outer wall 222 of attachment clip 216. The outer wall 221 is substantially tangential to the attachment clip 215 and substantially perpendicular to the first section 213 of connector. The outer wall 222 is substantially tangential to the attachment clip 216 and substantially perpendicular to the second section 214 of connector.

The first section 213 is attached to a stethoscope by a user at a first location on the stethoscope via the attachment clip 215 and the second section 214 is attached at a second location on the stethoscope via the attachment clip 216. The user attaches attachment clip 215 by gently forcing the section of the stethoscope at the first location on the stethoscope through the clip opening 219. The same operation is repeated for attaching attachment clip 216 at the second location on the stethoscope using clip opening 220. FIG. 8 shows device 210 in a first configuration where the connector sections (213, 214) are unconnected.

Figure 9:
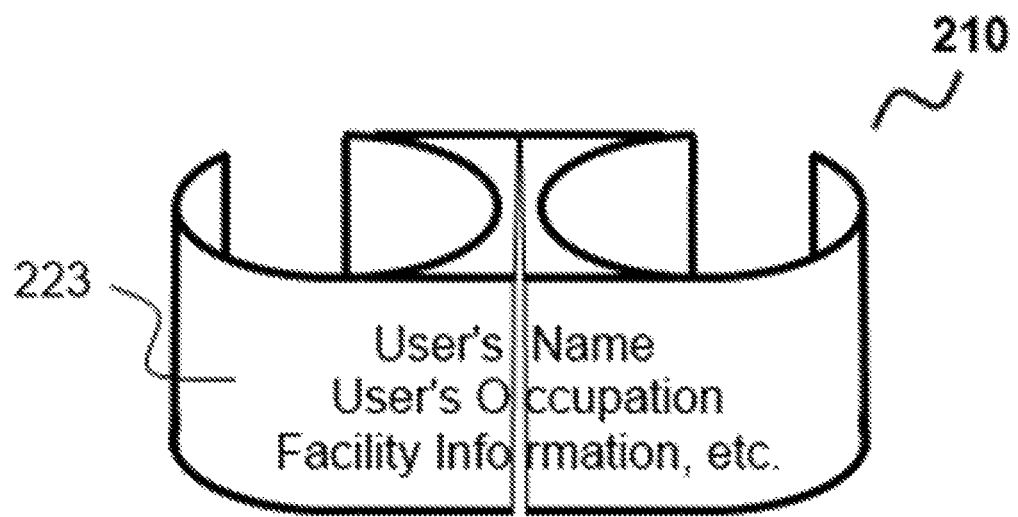
FIG. 9 shows a perspective view of the invention of FIG. 8 in a connected position, wherein sample text is visible on the substantially tangential outer wall.

FIG. 9 shows device 210 in a second configuration wherein first section 213 and second section 214 are connected. In the second configuration, outer walls 221 and 222 will be coplanar and adjacent. The combined surface area of outer walls 221 and 222 is an ideal location for the placement of text, images, and other information useful to the owner or user of the stethoscope. See sample text 223 on device 210 in FIG. 9.

There are many well known methods of attachment and many well know fastener types that would be readily apparent to one having ordinary skill in the art. Each may be a suitable replacement or substitution for the other, or there may be inherent advantages to one method of attachment and fastener type depending on the situation. Still referring to device 210, take as example and not limitation the following construction: the connector could be a simple pair of magnetic disks; the attachment clip and retaining layer could be constructed of a durable plastic, wood, or metal material; and the retaining layer could be formed into the attachment clip or glued, soldered, welded, fused, screwed, etc. onto the attachment clip.

Figure 10:
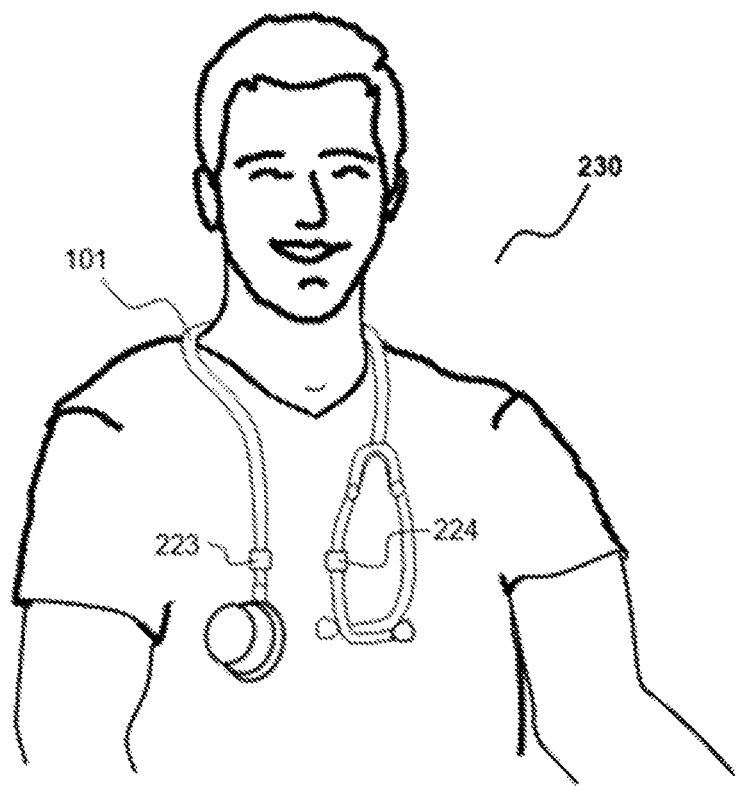
FIG. 10 shows a user wearing a stethoscope draped over the user's shoulder and behind the user's neck, wherein the stethoscope is equipped with an embodiment of the invention that is in the unconnected position.
Figure 11:
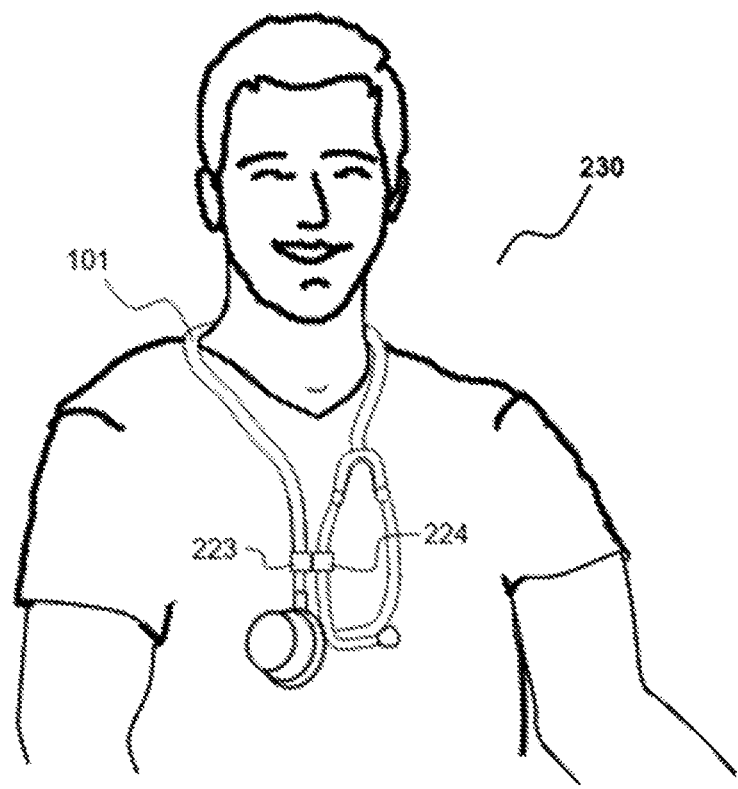
FIG. 11 shows a user wearing a stethoscope draped over the user's shoulder and behind the user's neck, wherein the stethoscope is equipped with an embodiment of the invention positioned on the stethoscope such that one piece of the connector is on a section of the stethoscope tube and the other piece is on an arm of the binaural, further wherein the connector is in the connected position.

Referring now to FIG. 10 and FIG. 11, a device 230 is used as a stand-in for any of the various possible embodiments of this invention, whether or not it has been disclosed expressly above.

Referring now to FIG. 10, the device 230 is in a first configuration wherein a first section 223 of a connector is not connected to a second section 224 of said connector. The first section 223 is attached to a first location on the stethoscope's tube that has been draped over a user's shoulders and behind the user's neck. The second section 224 is attached to a second location on the stethoscope's binaural between the eartip and the sound conductor.

Referring now to FIG. 11, the device 230 is in a second configuration wherein the first section 223 of a connector is connected to a second section 224 of said connector, forming a closed loop around the user's neck.

Referring now to FIG. 12, FIG. 13, and FIG. 14, a device 250 is used as a stand-in for any of the various possible embodiments of this invention, whether or not it has been disclosed expressly above.

Referring now to FIG. 12, the device 250 is in a first configuration wherein a first section 253 of a connector is not connected to a second section 254 of said connector. The first section 253 is attached to a first location on the stethoscope's tube that has been draped over a user's shoulders and behind the user's neck. The second section 254 is attached to a second location the stethoscope's tube.

Referring now to FIG. 13, the device 250 is in a second configuration wherein the first section 253 of a connector is connected to a second section 254 of said connector, forming a closed loop around the user's neck. The relative distance from the first location to the second location along the stethoscope tube can be adjusted by the user. FIG. 13 shows the user has chosen a relatively loose fitting, by attaching the connector sections (253, 254) at a large relative distance from one another along the tube, thereby forming a large closed loop. But see FIG. 14 which shows the user has chosen a relatively tight fitting, by attaching the connector sections (253, 254) at a relatively smaller distance from one another along the tube, compared to the locations of FIG. 13, thereby forming a smaller closed loop.

Referring now to FIG. 15 and FIG. 16, stethoscope securing device 300 comprises a reversibly connectable connector comprising a first section 1505; a second section 1506; a first attachment member 1510 coupled to the first section 1505, wherein the first attachment member 1510 has a first aperture 1515 configured to pass a first cable tie 1520; a second attachment member 1511 coupled to the second section 1506, wherein the second attachment member 1511 has a second aperture 1516 configured to pass a second cable tie 1521; a first magnet 1525 coupled to the first section 1505; and a ferrous plate 1526 coupled to the second section 1506. In some embodiments, a screw 1530 is used to secure the first magnet 1525 to the first section 1505. In some embodiments, a second screw (not visible) is used to secure the ferrous plate 1526 to the second section 1506. In some embodiments, the ferrous plate 1526 comprises a second magnet configured to couple to the first magnet. The cable tie may comprise any type of zip tie or the like.

The attachment bands and clips of the various embodiments described above may be made out of many suitable materials. In another embodiment not seen in the drawings, the attachment bands of each section of the connector do not require a band fastener because they are self coiling (such as a slap bracelet band). In another embodiment, the attachment band has an adhesive on at least one inward facing surface so that the attachment band can self adhere or adhere to the surface of the stethoscope. In another embodiment, the attachment band is a closed loop having elastic properties, such that the loop can be slipped over an end of the stethoscope. In another embodiment, the attachment band is a closed loop that can be slipped onto the stethoscope only when the stethoscope is at least partially unassembled. In another embodiment, the device is formed into the stethoscope during manufacturing or assembly.

In another embodiment, not shown in the drawings, the device is further comprising an integrated circuit and an antenna for passive radio frequency identification (RFID). In another embodiment, not shown in the drawings, the device is further comprising an integrated circuit, a battery, and an antenna for active radio frequency identification. A hospital or other such facility could use the embedded RFID to better manage, track, and locate stethoscopes and other instruments on which the device is attached. In another embodiment, not shown in the drawings, the device is further comprising an integrated circuit, a battery, and a radio antenna for Bluetooth standard communication. The Bluetooth would help the user locate misplaced or stolen stethoscopes and other instruments on which the device is attached. The Bluetooth functionality could also be used to allow the wearer to receive alerts or other communications from mobile phones, computers, hospital communications, patients, or hospital equipment.

In another embodiment of the invention, the device is further comprised of a light emitting electronic component, such as an LED. In another embodiment of the invention, the device is further comprised of a sound emitting electronic component, such as a speaker. In another embodiment of the invention, the device is further comprised of a sound receiving electronic component, such as a microphone. In another embodiment of the invention, the device is further comprised of a vibration creating electronic component, such as an unbalanced weight on a motor. In another embodiment of the invention, the device is further comprised of a display screen capable of displaying electronic or chemically created images. The added functionality of each of the above components could also be used to allow the wearer to receive alerts or other communications from mobile phones, computers, hospital communications, patients, or hospital equipment.

Although the invention has been described and illustrated with a certain degree of detail or with reference to one or more particular embodiments, it is understood that the present disclosures have been made only by way of example. It should be understood that the invention is not intended to be limited to the particular forms disclosed. Furthermore, the invention is amenable to various modifications and alternative forms. Obvious variations and other various changes in the composition, combination, and arrangement of parts can be utilized to by those skilled in the art without departing from the spirit and scope of the invention, as herein disclosed and claimed.

The invention claimed is:

1. A device for securing a stethoscope comprising:
a reversibly connectable connector comprising a first section and a second section;
a first attachment member coupled to the first section, wherein the first attachment member attaches to a first location on the stethoscope with a first cable tie; and
a second attachment member coupled to the second section, wherein the second attachment member attaches to a second location on the stethoscope with a second cable tie;
wherein the first section and the second section are reversibly connected together to secure the stethoscope around a user's neck.

2. The device of claim 1 further comprising a first magnet coupled to the first section and a ferrous plate coupled to the second section.

3. The device of claim 1 further comprising a first magnet coupled to the first section and a second magnet coupled to the second section.

4. The device of claim 1 wherein:
a plane passing through the connector substantially divides the first section from the second section when the two are in a connected configuration;
the first attachment member further comprises a first inner wall substantially defined by a first loop and a first outer sidewall that is at least partially tangential to the first loop and substantially perpendicular to the said plane passing through the connector; and
the second attachment member further comprises a second inner wall substantially defined by a second loop and a second outer sidewall that is at least partially tangential to the second loop, is substantially perpendicular to the said plane passing through the connector, and is substantially coplanar and adjacent to the said first outer sidewall when the first section and the second section are in the connected configuration.

5. The device of claim 1 further comprising visual information displayed on an outer sidewall of the device.

6. The device of claim 1 further comprising:
a passive radio frequency identification (RFID) component comprising an antenna and an integrated circuit.

7. The device of claim 1 further comprising:
an active radio frequency identification (RFID) component comprising a battery, an antenna, and an integrated circuit.

8. The device of claim 1 further comprising:
a Bluetooth Standard compliant electronic component comprising a battery, a radio antenna, and an integrated circuit.

9. The device of claim 1 further comprising:
a visible indicator light.

10. The device of claim 1 further comprising:
an audible sound producing electronic component.

11. The device of claim 1 further comprising:
a sound receiving electronic component.

12. The device of claim 1 further comprising:
a vibration producing electronic component.

13. The device of claim 1 further comprising:
an electronic display screen component.

14. A stethoscope comprising:
a reversibly connectable connector comprising a first section and a second section; wherein the first section is attached with a first cable tie to a first location on the stethoscope; wherein the second section is attached with a second cable tie to a second location on the stethoscope; and wherein the first section and the second section are reversibly connected together to secure the stethoscope around a user's neck.

* * * * *